United States Patent [19]

Agui et al.

[11] 4,008,237

[45] Feb. 15, 1977

[54] 2,3,5,8-TETRAHYDRO-5-ALKOXY-8-OXOFURO (2,3-g) QUINOLINE-7-CARBOXYLIC ACID DERIVATIVES

[75] Inventors: Hideo Agui, Toyoyaka; Iwao Nakatsuka, Nishinomiya; Toru Mitani, Kyoto; Mitsuo Nakashita, Kobe; Takenari Nakagome, Nishinomiya; Toshiaki Komatsu, Takarazuka; Akio Izawa; Yasuko Eda, both of Toyonaka, all of Japan

[73] Assignee: Sumitomo Chemical Company, Limited, Osaka, Japan

[22] Filed: Oct. 28, 1975

[21] Appl. No.: 626,001

Related U.S. Application Data

[63] Continuation-in-part of Ser. No. 379,888, July 16, 1973, abandoned.

[30] Foreign Application Priority Data

July 14, 1972 Japan .............................. 47-71132

[52] U.S. Cl. ..................... 260/287 AN; 260/287 L; 260/287 CF; 424/258
[51] Int. Cl.² ...................................... C07D 215/56
[58] Field of Search ............... 260/287 AN, 287 CF

[56] References Cited

UNITED STATES PATENTS 3,287,458  11/1966  Kaminsky et al. .......... 260/287 AN
3,506,667  4/1970  Kaminsky ................... 260/287 AN
3,753,993  8/1973  Lesher ......................... 260/287 AN
3,773,769  11/1973  Albrecht ...................... 260/287 AN
3,799,930  3/1974  Nakagome et al. ......... 260/287 AN

*Primary Examiner*—Donald G. Daus
*Assistant Examiner*—David E. Wheeler
*Attorney, Agent, or Firm*—Sughrue, Rothwell, Mion, Zinn & Macpeak

[57] ABSTRACT

Novel antibacterial agents consisting of a 2,3,5,8-tetrahydro-5-alkoxy-8-oxofuro(2,3-g)quinoline-7-carboxylic acid of the formula:

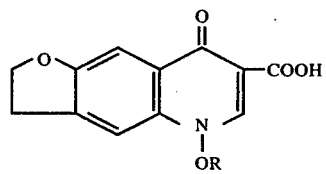

wherein R is $C_1$–$C_4$ alkyl, a process for producing the derivatives and pharmaceutical compositions containing the same. The above-identified derivatives possess antibacterial activity against gram-negative bacteria at test concentration levels of about 0.0001 to 1.0 mg/cc.

2 Claims, No Drawings

2,3,5,8-TETRAHYDRO-5-ALKOXY-8-OXOFURO(2,3-g)QUINOLINE-7-CARBOXYLIC ACID DERIVATIVES

CROSS-REFERENCE TO RELATED APPLICATIONS

This application is a continuation-in-part of copending application Ser. No. 379,888, filed July 16, 1973, in the names of Hideo Agui et al., now abandoned.

BACKGROUND OF THE INVENTION

1. Field of the Invention

This invention relates to novel antibacterial agents. More particularly, it pertains to 2,3,5,8-tetrahydro-5-alkoxy-8-oxofuro(2,3-g)quinoline-7-carboxylic acids, to a process for preparing such compounds and to therapeutic compositions containing the above described compounds which are useful in the treatment of bacterial infections.

2. Description of the Prior Art

Some quinoline carboxylic acid-type compounds are disclosed to have antibacterial activity in U.S. Pat. Nos. 3,506,667 and 3,799,930.

SUMMARY OF THE INVENTION

We have found that a novel 2,3,5,8-tetrahydro-5-alkoxy-8-oxofuro(2,3,-g)quinoline-7-carboxylic acids of the formula:

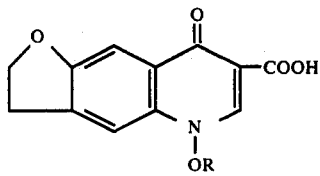

wherein R is $C_1$–$C_4$ alkyl, and the salts thereof, have excellent antibacterial properties.

DETAILED DESCRIPTION OF THE INVENTION

One object of the present invention is to provide novel 2,3,5,8-tetrahydro-5-alkoxy-8-oxofuro(2,3-g)quinoline-7-carboxylic acids which are useful as antibacterial agents, as well as pharmaceutically compatible salts thereof.

Another object of the invention is to provide a process for producing such antibacterial agents.

Still another object of the invention is to provide a pharmaceutical composition.

A further object of the invention is to provide a method for controlling bacteria.

Other objects and advantages of the present invention will be apparent from the following description.

In order to accomplish these objects, the present invention provides the compound of formula (I) given above.

The present invention further provides a process for producing the compound of formula (I), which consists of (1) reacting a compound of the general formula:

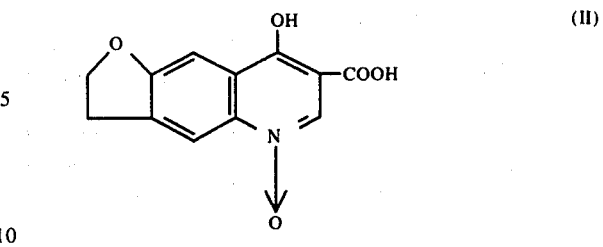

with an organic ester of a strong acid, and if desired, hydrolyzing the resulting ester; or (2) heating a compound represented by the general formula:

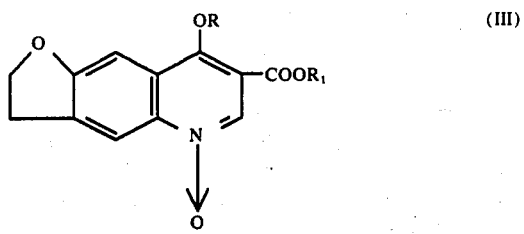

wherein R is the same as defined with respect to formula (I) and $R_1$ is $C_1$–$C_4$ alkyl, in the presence of an acid catalyst or an organic ester of a strong acid, and hydrolyzing the resulting ester.

According to a further aspect of the invention, there are provided pharmaceutical compositions consisting of a pharmaceutically effective amount of the compound of formula (I) given above and a pharmaceutically acceptable carrier or diluent.

According to a still further aspect of the invention, there is provided a method for controlling bacteria, which consists of contacting bacteria with a compound of formula (I) given above.

According to the process of the invention, novel compounds of formula (I) can be obtained by reacting a compound of formula (II) with an organic ester of a strong acid, i.e., an acid which is substantially completely dissociated in an aqueous solution.

As used herein, the term organic esters refers to compounds of the formula:

RY      (IV)

wherein R is the same as defined with respect to formula (I), Y is the anionic portion of a strong inorganic acid or an organic sulfonic acid, e.g., chloride, bromide, iodide, sulfate, benzenesulfonate, para-toluenesulfonate, diethyloxonium fluoroborate and the like. The chloride, bromide, iodide or sulfate are preferred because of their ready availability. The reaction is preferably carried out in the presence of an acid-acceptor. The acid-acceptor is a basic substance which preferably forms highly water-soluble by-products which are easily separable from the product of the reaction, including, for example, sodium hydroxide, potassium hydroxide, sodium carbonate, potassium carbonate, sodium alkoxides, potassium alkoxides, sodium amide, sodium hydride and the like. The purpose of the acid-acceptor is to take up the acid (HX) which is split out during the course of the reaction. The reaction can be carried out in the presence or in the absence of a suitable solvent, but preferably is carried out in a solvent such as water, a lower-alkanol, acetone, dioxane, dimethylformamide, or a mixture thereof (e.g., a mixture of water and a lower alkanol).

The reaction is generally carried out at a temperature below 150° C, and may be controlled by cooling or heating.

When the compound of formula (II) is reacted with a large excess of an organic ester of a strong acid of formula (IV), an ester represented by the general formula:

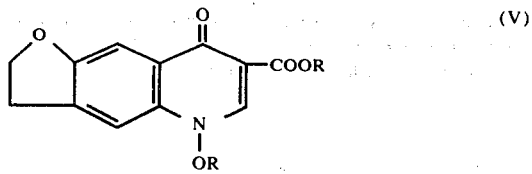

wherein R is the same as defined with respect to formula (I), is obtained. The ester of formula (V) is hydrolyzed to yield the corresponding free acid of formula (I). The hydrolysis in the present invention is conducted in accordance with conventional procedures as are usually employed in the hydrolysis of ester compounds. In the present invention, the ester compound is reacted with water, and the hydrolysis is preferably carried out in the presence of an acidic compound such as an inorganic acid (e.g., hydrochloric acid, sulfuric acid, etc.) or an alkaline compound such as an alkali metal hydroxide, etc.

In another process aspect of the invention, a compound of general formula (III) is heated in the presence of or in the absence of an acid catalyst or an organic ester of a strong acid, and the product is further hydrolyzed, whereby the compound of formula (I) is obtained.

For rearrangement, the starting material may simply be melted upon heating, but a solvent inert to the reaction, such as toluene, benzene, xylene, diphenyl, diphenyl ether, a mineral oil, a petroleum hydrocarbon, an alcohol, dioxane, dimethylformamide, a halogenated hydrocarbon or a mixture thereof may be used. The reaction is conducted at a temperature of from 50° to 300° C, preferably from 100° to 250° C. The reaction proceeds upon heating either in the presence of or in the absence of a solvent, but when the reaction is conducted in the presence of an organic ester represented by formula (IV), such as an alkyl halide, a dialkyl sulfate, an alkyl p-toluenesulfonate, or triethyloxonium fluoroborate, or in the presence of an acid catalyst, the reaction is promoted and the objective compound can be obtained in high yield, even under mild conditions.

Examples of the acid catalyst used in the above reaction include an inorganic acid such as a hydrogen halide, an organic acid such as p-toluenesulfonic acid or acetic acid, and a Lewis acid such as aluminium chloride or boron trifluoride. When the above described promotors are used, the reaction is effected at a temperature from 20° to 250° C, preferably from 20° to 150° C.

The compound represented by general formula (I) is prepared from the compound of general formula (V) by subjecting the compound of general formula (V) to hydrolysis.

The compounds of formula (III) can be prepared by the reaction of compounds of the formula:

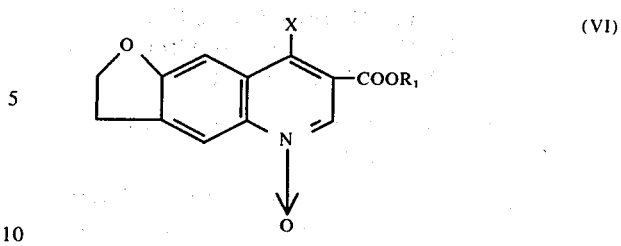

wherein X is a halogen atom and $R_1$ is as defined above, with an alcohol represented by the general formula ROH, wherein R is the same as defined with respect to formula (I). In this case, it is preferred to conduct the reaction in the presence of an acid-acceptor.

Examples of suitable acid-acceptors used in this reaction are inorganic or organic basic materials, such as an alkali metal hydroxide, an alkali metal carbonate, an alkali metal bicarbonate or a metal salt of the alcohol represented by the formula ROH. The use of a metal salt of the alcohol is most preferred. Moreover, to insure that the reaction proceeds smoothly, a solvent can be employed. Illustrative solvents are solvents which are inert to the reaction, such as benzene, toluene, petroleum benzin and ether. Further, an alcohol represented by the general formula ROH may also be used. When a large amount of such an alcohol is used, occasionally an ester-exchange reaction of the alkoxycarbonyl group at the 7-position occurs, which results in the formation of the 8-alkoxy ester having general formula (III) in which R contains the same alkyl group as $R_1$.

While the reaction of the present invention proceeds even at low temperatures, it may also be conducted by heating the system to temperatures lower than 200° C.

The compound of formula (III) can also be prepared by the reaction of a compound of the formula:

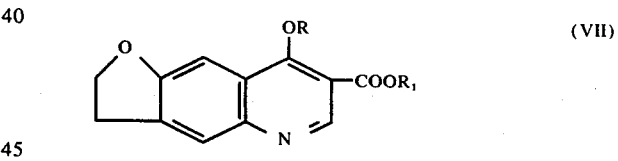

wherein R and $R_1$ are as defined above, with a peroxide.

Examples of such peroxides include a peracid, e.g. performic acid, peracetic acid, a halogenated peracetic acid such as pertrifluoroacetic acid, perpropionic acid, perlactic acid, monopermaleic acid, monopersuccinic acid, perbenzoic acid, a substituted perbenzoic acid such as monoperphthalic acid and 3-chloroperbenzoic acid, diperphthalic acid, percamphoric acid and hydrogen peroxide or a mixture thereof. Among these peroxides, performic acid, peracetic acid, monopermaleic acid, perbenzoic acid, monoperphthalic acid, 3-chloroperbenzoic acid and hydrogen peroxide are particularly preferred. The reaction proceeds smoothly at a temperature between −50° and 150° C.

Generally, the reaction is conducted at room temperature or while cooling. As a solvent, there can be used an excess of the parent acid or an anhydride of the peracid (e.g. acetic acid with peracetic acid), or any unreactive solvent (e.g. water, an ether, benzene, a halogenated hydrocarbon such as chloroform, dichloroethane and chlorobenzene). The peroxide is used in an amount of one or more molecular equivalents to the compound of formula (VII), but the use of a large amount of the peroxide does not hinder the progress of the reaction.

The compounds of formula (VI) can be prepared by the oxidation of compounds of the formula:

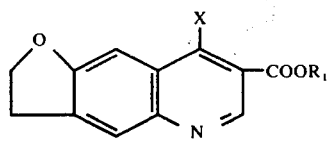

(VIII)

wherein X and $R_1$ are as defined above, with a peroxide.

This oxidation can be carried out in the same manner as the reaction of compound (VII) with a peroxide.

As previously stated, the compounds of formula (I) are novel compounds, and are useful as antibacterial agents which have strong antibacterial activity, excellent pharmacokinetic properties, and low toxicity. For example, when tested by conventional in vitro bacteriological evaluation procedures, the compounds of formula (I) have been found to possess antibacterial activity against Gram-negative bacteria such as *Escherichia coli* and *Proteus mirabilis* at test concentration levels in the range of about 0.0001 to 1.0 mg/cc.

In toxicological investigations including macroscopic examination and urinalysis for pH, protein, occult blood and the like, no significant symptoms or abnormalities were observed in 6-week-old female rats of the Sprague-Damley-SLC strain which received a compound of formula (I) at dose levels of 1000 to 2000 mg/Kg/day for 9 days. Moreover, the compounds of formula (I) were distributed in serum as well as in urine at a high concentration, and are, therefore, particularly suitable for the treatment of urinary tract infections.

For the treatment of bacterial infectious disease caused by Gram-negative bacteria in mammals such as rats, mice, dogs, cats, humans, and the like, the compounds of formula (I) are preferably orally administered at a dose of about 30 to 70 mg/Kg of body weight daily in conventional pharmaceutical form such as in tablet, powder or like form. Such compositions are generally administered 1 to 4 times daily.

Pharmaceutical compositions containing the compounds of formula (I) as an active ingredient can be prepared by admixing the compounds of formula (I) with known pharmaceutical carriers, for example, lactose, mannitol, starch and the like using conventional procedures.

The invention will now be described in further detail by the following Examples which are given for illustrative purposes only and are not intended to limit the invention.

EXAMPLE 1

A mixture containing 33 g of 5[2,2-bis(ethoxycarbonyl) vinylamino]-2,3-dihydrobenzofuran and 330 ml of phosphorus oxychloride was refluxed for 2 hours. After the reaction was completed, excess phosphorus oxychloride was distilled off under reduced pressure. Ice water was added to the obtained residue. The resulting mixture was rendered alkaline to pH 8 by the addition of an aqueous sodium bicarbonate solution and then extracted with ethyl acetate.

The extract was washed with water, dried over sodium sulfate and evaporated to give 29.5 g of a dark red solid containing ethyl 9-chloro-1,2-dihydrofuro(3,2-f)quinoline-8-carboxylate and ethyl 8-chloro-2,3-dihydrofuro(2,3-g)quinoline-7-carboxylate.

The former was removed by elution through a silica gel column using isopropyl ether. The latter was purified using ethyl acetate as the eluent to give 14.6 g (50%) of yellow prisms having a melting point of 85°–87° C. Elementary analysis values for $C_{14}H_{12}O_3NCl$ were as follows:

|  | C(%) | H(%) | N(%) | Cl(%) |
|---|---|---|---|---|
| Calculated | 60.55 | 4.36 | 5.04 | 12.77 |
| Found | 60.26 | 4.45 | 4.98 | 12.56 |

EXAMPLE 2

A mixture containing 12.6 g of ethyl 8-chloro-2,3-dihydrofuro(2,3-g)quinoline-7-carboxylate, 150 ml of methylene chloride and 14.6 g of m-chloroperbenzoic acid (purity: 80%) was stirred at 5°–10° C for 3 hours, and then stirred at room temperature for 15 hours. After the reaction was completed, 60 ml of a 20% aqueous sodium bicarbonate solution was added to the reaction mixture.

The methylene chloride layer was separated, washed with water and distilled off under reduced pressure. The resulting solid was washed with ethyl acetate to give 12 g (91%) of ethyl 8-chloro-2,3-dihydrofuro (2,3-g)quinoline-7-carboxylate N-oxide as yellow prisms having a melting point of 160°–162° C (decomposition). Elementary analysis values for $C_{14}H_{12}O_4NCl$ were as follows:

|  | C(%) | H(%) | N(%) |
|---|---|---|---|
| Calculated | 57.25 | 4.12 | 4.77 |
| Found | 57.34 | 4.12 | 4.72 |

EXAMPLE 3

A mixture containing 12 g of ethyl 8-chloro-2,3-dihydrofuro(2,3-g)quinoline-7-carboxylate, 100 ml of water, 10.9 g of 85% potassium hydroxide and 80 ml of methanol was stirred while refluxing for 2 hours. The methanol was evaporated at atmospheric pressure. The resulting mixture was heated to 90°–95° C and stirred for one further hour. Then, the mixture was acidified to pH 2 by the addition of 6N hydrochloric acid at 80° C. After cooling, the resulting white precipitate was filtered and washed with water to give 10.03 g (99%) of 2,3,5,8-tetrahydro-5-hydroxy-8-oxofuro(2,3-g)-quinoline-7-carboxylic acid as pale yellow prisms having a melting point of 274°–275° C (decomposition). Elementary analysis values for $C_{12}H_9O_5N$ were as follows:

|  | C(%) | H(%) | N(%) |
|---|---|---|---|
| Calculated | 58.30 | 3.67 | 5.62 |
| Found | 58.33 | 3.58 | 5.72 |

EXAMPLE 4

A mixture containing 10 g of 2,3,5,8-tetrahydro-5-hydroxy-8-oxofuro(2,3-g)quinoline-7-carboxylic acid, 9.4 g of 85% potassium hydroxide, 400 ml of water, 300 ml of ethanol and 46 g of methyl iodide was stirred at 35°–40° C for 15 hours. 300 ml of water was added to the reaction mixture. The mixture was acidified to pH 1 by the addition of 6N hydrochloric acid and stirred at 90° C for 1 hour. The white precipitate which formed was filtered and washed with water.

Recrystallization from dimethylformamide gave 9 g of 2,3,5,8-tetrahydro-5-methoxy-8-oxofuro(2,3-g)quinoline-7-carboxylic acid as colorless needles having a melting point of 270°–270.5° C (decomposition). Elementary analysis values for $C_{13}H_{11}O_5N$ were as follows:

|            | C(%)  | H(%) | N(%) |
|------------|-------|------|------|
| Calculated | 59.77 | 4.24 | 5.36 |
| Found      | 59.83 | 4.00 | 5.25 |

While the invention has been described in detail and with reference to the specific embodiments thereof, it will be apparent to one skilled in the art that various changes and modifications can be made therein without departing from the spirit and scope thereof.

What is claimed is:
1. A compound of the formula:

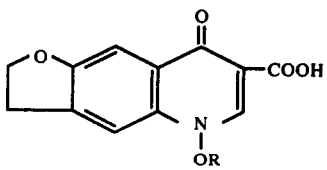

wherein R is $C_1$–$C_4$ alkyl, and nontoxic pharmaceutically acceptable salts thereof.

2. A compound of the formula:

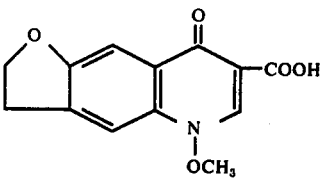

* * * * *